US008238628B2

(12) United States Patent
Kazuno et al.

(10) Patent No.: US 8,238,628 B2
(45) Date of Patent: Aug. 7, 2012

(54) IMAGING DIAGNOSIS SUPPORTING SYSTEM AND IMAGING DIAGNOSIS SUPPORTING METHOD

(75) Inventors: Muneyasu Kazuno, Nasushiobara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 840 days.

(21) Appl. No.: 12/100,780

(22) Filed: Apr. 10, 2008

(65) Prior Publication Data

US 2008/0253629 A1 Oct. 16, 2008

(30) Foreign Application Priority Data

Apr. 12, 2007 (JP) ................. 2007-105330

(51) Int. Cl.
*G06K 9/00* (2006.01)
*G06K 9/60* (2006.01)

(52) U.S. Cl. .................. 382/128; 382/305
(58) Field of Classification Search .......... 382/128, 382/305
See application file for complete search history.

(56) References Cited

U.S. PATENT DOCUMENTS

| 6,247,004 | B1* | 6/2001 | Moukheibir | 706/46 |
| 6,520,912 | B1* | 2/2003 | Brooks et al. | 600/437 |
| 7,698,246 | B2* | 4/2010 | Friedlander et al. | 706/47 |
| 2004/0086163 | A1* | 5/2004 | Moriyama et al. | 382/131 |
| 2004/0167802 | A1* | 8/2004 | Takada et al. | 705/2 |
| 2006/0123002 | A1* | 6/2006 | Hornegger et al. | 707/6 |
| 2007/0239489 | A1 | 10/2007 | Masuzawa et al. | |
| 2008/0146943 | A1* | 6/2008 | Jenkins et al. | 600/466 |
| 2008/0201372 | A1 | 8/2008 | Fukatsu et al. | |
| 2008/0212854 | A1 | 9/2008 | Fukatsu et al. | |

FOREIGN PATENT DOCUMENTS

| JP | 2003-337861 A | 11/2003 |
| JP | 2004-30555 A | 1/2004 |
| JP | 2004-254952 A | 9/2004 |
| JP | 2004-344314 | 12/2004 |
| JP | 2005-63080 A | 3/2005 |
| JP | 2006-18817 A | 1/2006 |
| JP | 2006-319356 | 11/2006 |
| JP | 2007-167634 | 7/2007 |

OTHER PUBLICATIONS

U.S. Appl. No. 12/107,356, filed Apr. 22, 2008, Kazuno, et al.
U.S. Appl. No. 12/246,117, filed Oct. 6, 2008, Yamagishi, et al.
U.S. Appl. No. 12/260,395, filed Oct. 29, 2008, Futami, et al.
Japanese Office Action mailed on Apr. 3, 2012, issued for JP Application No. 2007-105330, filed on Apr. 12, 2007 (with English translation).

* cited by examiner

*Primary Examiner* — Bhavesh Mehta
*Assistant Examiner* — Utpal Shah
(74) *Attorney, Agent, or Firm* — Oblon, Spivak, McClelland, Maier & Neustadt, L.L.P.

(57) ABSTRACT

In a server apparatus, an information classification is determined by a user and a utilization situation, and provision information is determined on the basis of the determined information classification. A common object is processed to include only the determined provision information, and then provided to a client apparatus. To the client apparatus, a common object including requisite minimum information is provided.

22 Claims, 11 Drawing Sheets

FIG. 2

| USER ID | APPLICATION NAME | APPARATUS NAME | COMMON OBJECT | DISPLAY INFORMATION CLASSIFICATION |
|---|---|---|---|---|
| Dr. TARO | DicomViewer | INTERPRETATION TERMINAL 1 | NOT DISPLAY | — |
| Dr. TARO | COMMON OBJECT VIEWER | INTERPRETATION TERMINAL 1 | DISPLAY | ALL |
| Dr. HANAKO | COMMON OBJECT VIEWER | EXAMINATION TERMINAL 2 | DISPLAY | SCAN CONDITION 1 |
| ENGINEER A | COMMON OBJECT VIEWER | EXAMINATION TERMINAL 5 | DISPLAY | SCAN CONDITION 2 |
| ... | | | | |
| ⋮ | ⋮ | ⋮ | ⋮ | ⋮ |

FIG. 3

| DISPLAY INFORMATION CLASSIFICATION | POSITIONING IMAGE | SCAN RANGE | SCAN CONDITION | IMAGE GENERATING CONDITION | EXAMINATION HISTORY | INFORMATION ABOUT KEY IMAGE |
|---|---|---|---|---|---|---|
| ALL | ○ | ○ | ○ | ○ | ○ | ○ |
| SCAN CONDITION 1 | ○ | ○ | ○ | | ○ | |
| SCAN CONDITION 2 | | | ○ | | | |
| INTERPRETATION 1 | | | ○ | ○ | ○ | ○ |
| INTERPRETATION 2 | | | | ○ | ○ | |
| NONE | — | — | — | — | — | — |
| ... | ... | ... | ... | ... | ... | ... |

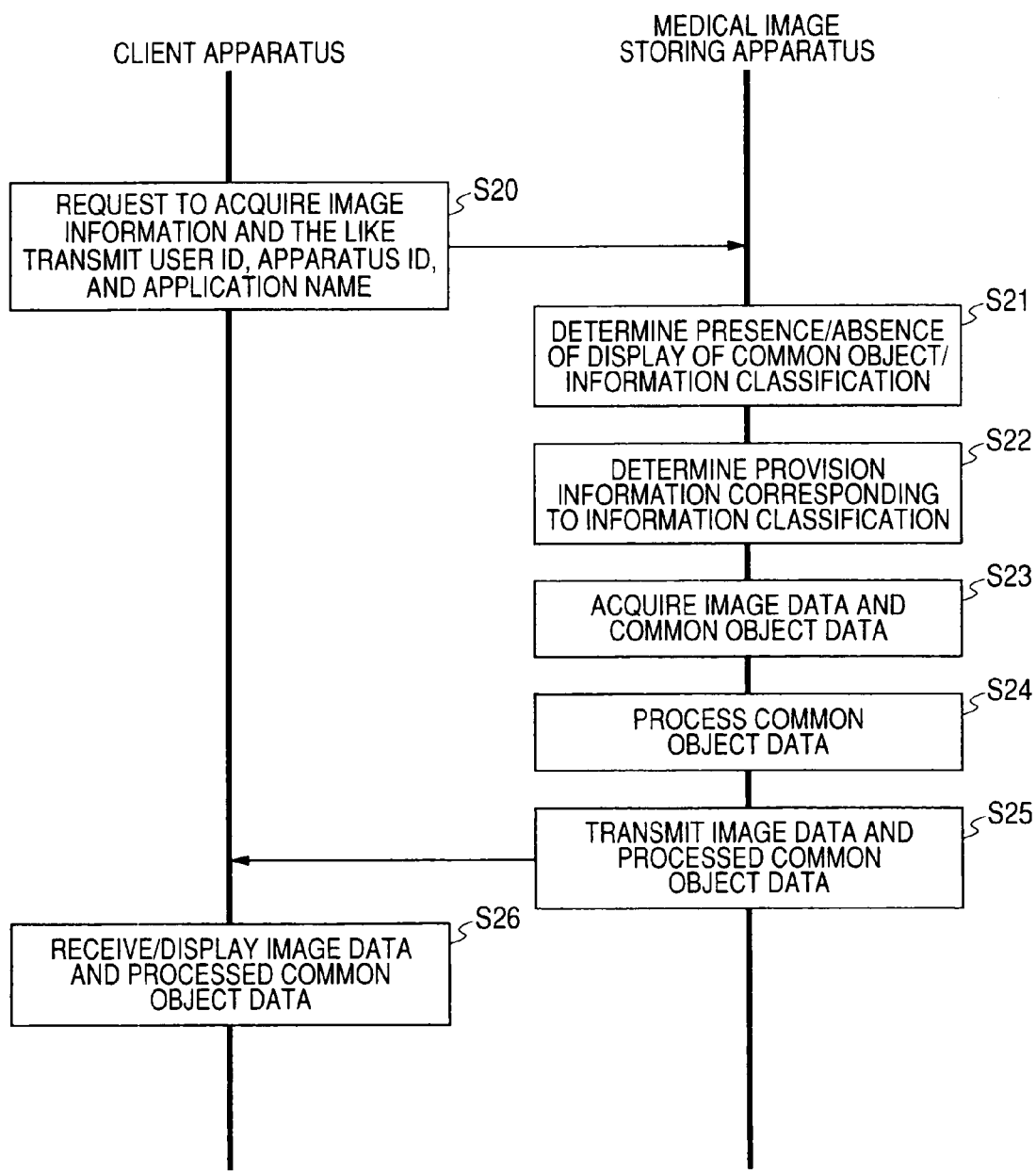

FIG. 7

| USER ID | APPLICATION NAME | APPARATUS NAME | COMMON OBJECT | DISPLAY INFORMATION CLASSIFICATION | GENERATION |
|---|---|---|---|---|---|
| Dr. TARO | DicomViewer | INTERPRETATION TERMINAL 1 | NOT DISPLAY | — | |
| Dr. TARO | COMMON OBJECT VIEWER | INTERPRETATION TERMINAL 1 | DISPLAY | ALL | SECOND GENERATION |
| Dr. HANAKO | COMMON OBJECT VIEWER | EXAMINATION TERMINAL 2 | DISPLAY | SCAN CONDITION 1 | THIRD GENERATION |
| ENGINEER A | COMMON OBJECT VIEWER | EXAMINATION TERMINAL 5 | DISPLAY | SCAN CONDITION 2 | THIRD GENERATION |
| ... | ... | ... | ... | ... | ... |

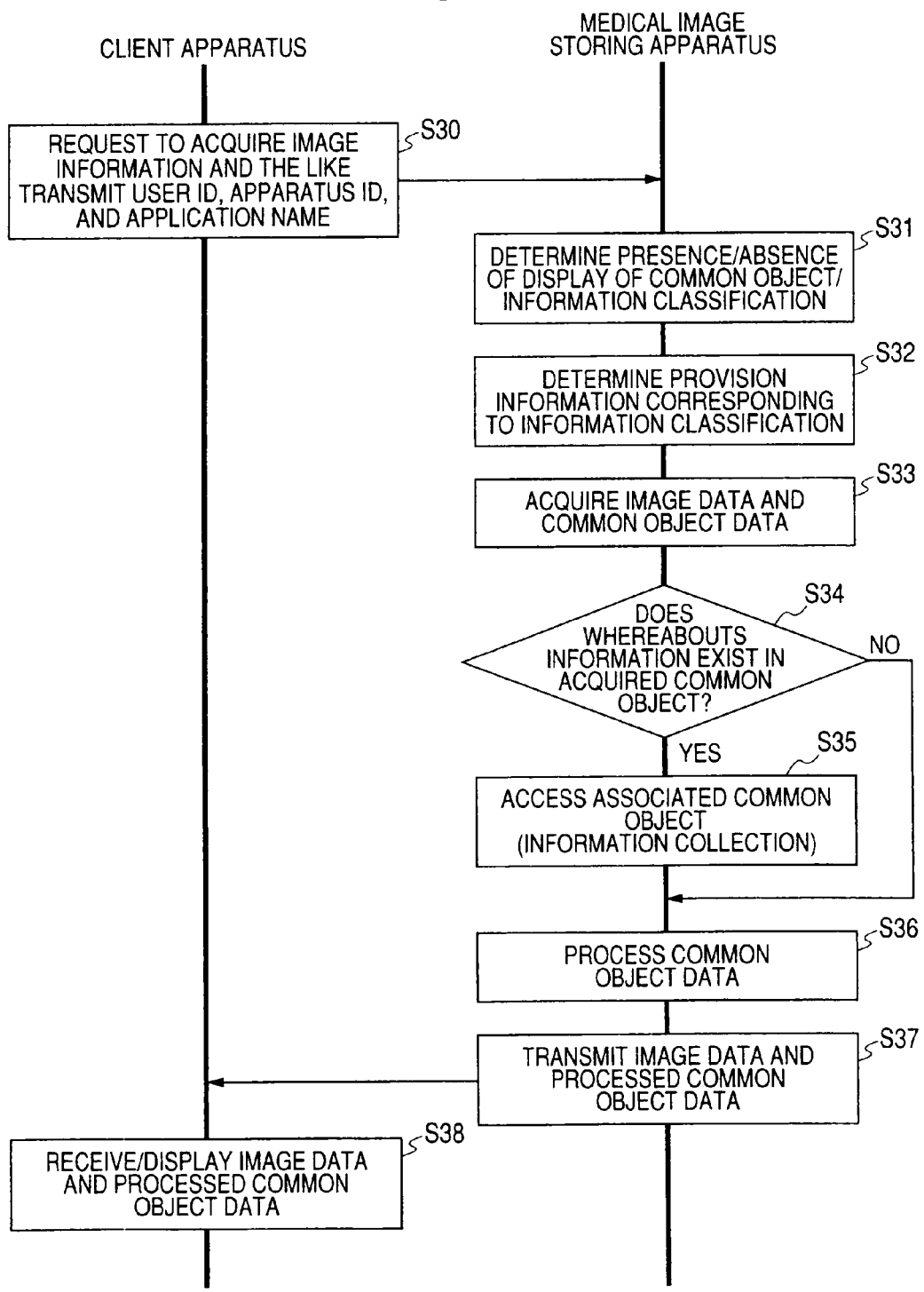

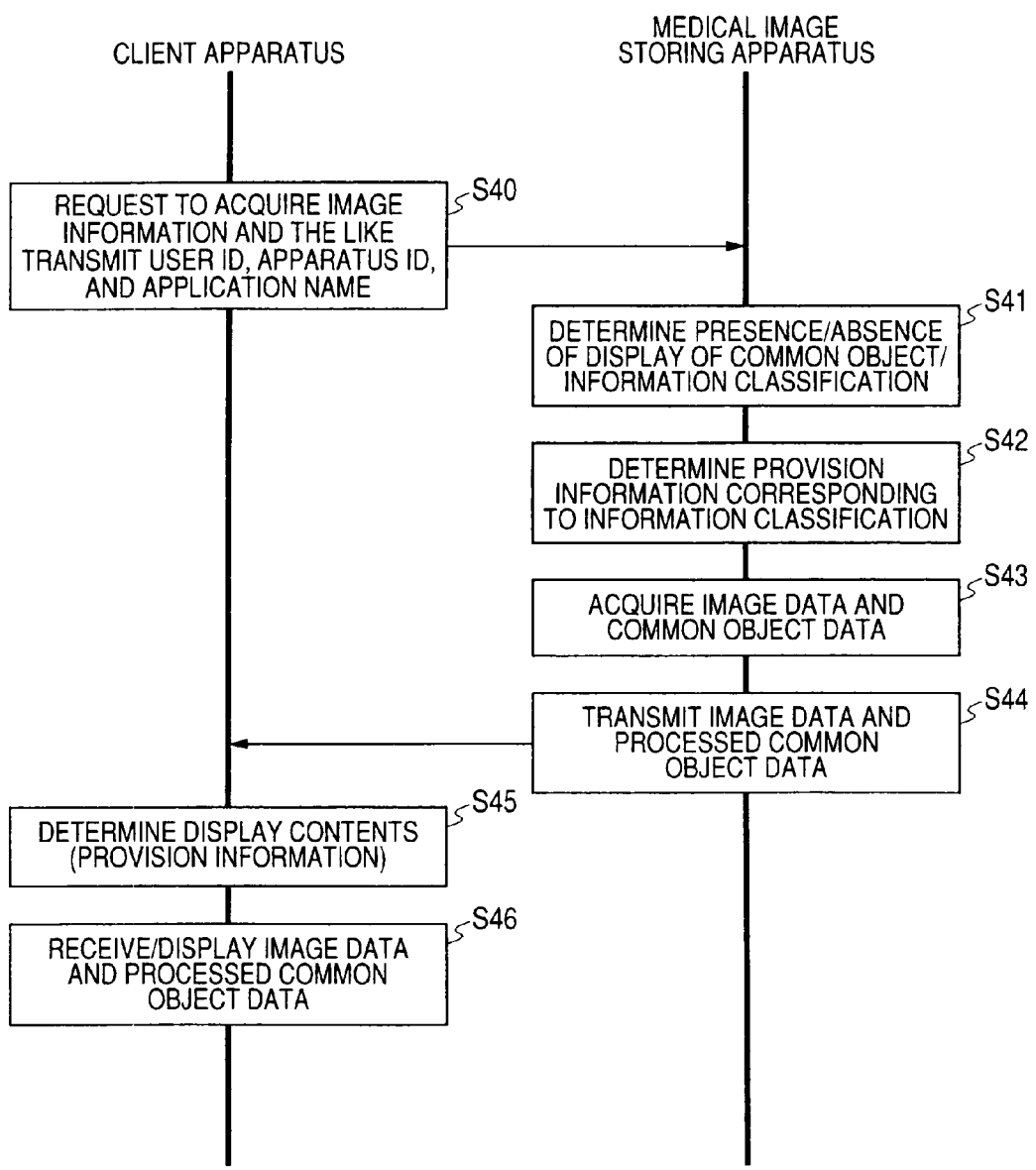

FIG. 11

| USER ID | APPLICATION NAME | APPARATUS NAME | KEY IMAGE | MEDICAL REPORT | COMMON OBJECT | DISPLAY INFORMATION CLASSIFICATION ABOUT COMMON OBJECT |
|---|---|---|---|---|---|---|
| Dr. TARO | DicomViewer | INTERPRETATION TERMINAL 1 | DISPLAY | DISPLAY | NOT DISPLAY | – |
| Dr. TARO | COMMON OBJECT VIEWER | INTERPRETATION TERMINAL 1 | NOT DISPLAY | DISPLAY | DISPLAY | ALL |
| Dr. HANAKO | COMMON OBJECT VIEWER | EXAMINATION TERMINAL 2 | NOT DISPLAY | DISPLAY | DISPLAY | SCAN CONDITION 1 |
| ENGINEER A | COMMON OBJECT VIEWER | EXAMINATION TERMINAL 5 | NOT DISPLAY | NOT DISPLAY | DISPLAY | SCAN CONDITION 2 |
| ... | ... | ... | ... | ... | ... | ... |

IMAGING DIAGNOSIS SUPPORTING SYSTEM AND IMAGING DIAGNOSIS SUPPORTING METHOD

CROSS-REFERENCE TO RELATED APPLICATIONS

This application is based upon and claims the benefit of priority from prior Japanese Patent Application No. 2007-105330, filed Apr. 12, 2007, the entire contents of which are incorporated herein by reference.

BACKGROUND OF THE INVENTION

1. Field of the Invention

The present invention relates to an imaging diagnosis supporting system and an imaging diagnosis supporting method that can determine whether or not to transmit medical information to a user, who requires medical information, and appropriately select corresponding contents when the medical information is transmitted, without deteriorating communication efficiency of a network, operation efficiency of each apparatus, and working efficiency during interpretation.

2. Description of the Related Art

In recent years, a medical activity is finely divided. For example, image diagnosis is divided into works of acquisition of diagnostic images of a patient, reading of the acquired diagnostic images and generation of a report, and explanation of the diagnosis result or treatment course based on the report. Each of the works is done by an expert (medical doctor or medical engineer), and a medical activity, such as diagnosis for a patient, is achieved by all of the works. Each of the experts executes his/her work on the basis of information generated by the other experts in the preceding works and by properly referring to diagnostic information in the past.

Each of the works is performed by a doctor's terminal, a medical imaging diagnosis apparatus, such as an X-ray CT (Computed Tomography) apparatus or an MRI (Magnetic Resonance Imaging) apparatus, which acquires diagnostic images, a PACS (Picture Archiving and Communication System) server (medical image storing apparatus), which stores the diagnostic images, an image viewing apparatus, which reads the diagnostic images, and an imaging diagnosis report creation supporting apparatus through a network. For example, an attending physician acquires information from the hospital information system (HIS) using his/her terminal, inputs required items while referring to an interpretation report, and generates an order (examination request) using the radiology information system (RIS). An engineer who operates a medical image diagnostic apparatus receives the generated order through the network, determines a scan range and a scan condition on the basis of the contents of the order, and collects required images. The acquired images are stored in the medical image storing apparatus through the network automatically or according to a predetermined operation. The image viewing apparatus or the imaging diagnostic report creation supporting apparatus acquires the images or past reports stored in the medical image storing apparatus, for example, for the purpose of the progress observation of the interpretation physician. In the imaging diagnostic report creation supporting apparatus, selection of an image (key image) as the ground of diagnosis and creation of a report are performed. The created report and the selected key image are transmitted to the medical image storing apparatus through the network and stored therein.

In recent years, as regards such an imaging diagnosis, in which the works are divided, Japanese Patent Application No. 2006-319356 has suggested a system that allows past examination information to be efficiently used. In this system, an object having, as the contents, a past scan condition, key image information, or past examination information, which was referred to during scan, is shared as information. Then, a user can see the key image or the scan condition, which was used in the past diagnosis, by referring to a common object with a predetermined apparatus at a predetermined timing. Accordingly, the user can reproduce the past examination with high precision and photograph an image suitable for comparative interpretation. In addition, as regards the examination while referring to the past, the reference history is also stored in the common object, and thus during interpretation, a comparative subject to be referred to can be automatically specified and displayed from the information, and a preparatory activity of the interpretation physician can be significantly reduced.

However, when the system, which uses a common object is introduced, for example, a display device (including a display client), which does not correspond to the common object handles the common object, similarly to usual image information. For this reason, for example, the following problems may occur.

That is, in the server apparatus, since the common object is handled, similarly to the usual image information, the common object itself, which is not needed in the client apparatus (for example, a viewer), may be transmitted. In this case, unnecessary data may be transmitted and acquired on the network, which results in deterioration of the communication efficiency of the network and the operation efficiency of each apparatus.

Furthermore, when the common object, which is not needed in the client apparatus, is displayed, a display area of an image (for example, a key image) required for interpretation becomes small. For this reason, an unnecessary work, such as deletion of some of the common object or the entire common object, may be performed, which results in deterioration of the working efficiency during interpretation.

In addition, when various kinds of information, such as a medical image report and image data, other than the common object, are transmitted/received between the server apparatus and the client apparatus through the network, the communication efficiency of the network, the operation efficiency of each apparatus, and the working efficiency during interpretation may be deteriorated.

BRIEF SUMMARY OF THE INVENTION

The invention has been finalized in consideration of the above-described problems, and it is an object of the invention to provide an imaging diagnosis supporting system and an imaging diagnosis supporting method that can appropriately transmit all or part of contents to a client apparatus, which requires medical information, such as a common object or a report, without deteriorating communication efficiency of a network, operation efficiency of each apparatus, and working efficiency during interpretation.

According to an aspect of the present invention, it is provided that an imaging diagnosis supporting system including: a storing unit which stores a plurality of objects each including at least one of a scan condition, a scan range, and the position of a key image as the ground of diagnosis, and an image; a receiving unit which receives, from a user, specific information of an examination to be referred to, and combinations of user identification information and utilization situation information; a determining unit which, on the basis of first determination information for determining whether to provide the objects to the user or not for each combination of the user identification information and the utilization situation information, determines whether or not to provide an object in the received combination; a collecting unit which, when the determining unit determines to provide the object, collects an object to be specified by the specific information of the examination from the storing unit; and a display unit that displays the object to be specified by the specific information of the examination.

According to another aspect of the present invention, it is provided that an imaging diagnosis supporting server including: a receiving unit which receives, from a user, specific information of an examination to be referred to, and combinations of user identification information and utilization situation information; a determining unit which, on the basis of determination information for determining whether to provide predetermined medical information among a plurality of medical information to the user or not for each combination of the user identification information and the utilization situation information, determines whether or not to provide medical information in the received combination; and a collecting unit which, when the determining unit determines to provide the medical information, collects the medical information to be provided from a storing unit, which stores a plurality of medical information, on the basis of the specific information of the examination.

According to yet another aspect of the present invention, it is provided that an imaging diagnosis supporting server including: a storing unit which stores a plurality of objects each including at least one of a scan condition, a scan range, and the position of a key image as the ground of diagnosis, and an image; a receiving unit which receives, from a user, specific information of an examination to be referred to, and combinations of user identification information and utilization situation information; a determining unit which, on the basis of first determination information for determining whether to provide the objects to the user or not for each combination of the user identification information and the utilization situation information, determines whether or not to provide an object in the received combination; and a collecting unit which, when the determining unit determines to provide the object, collects an object to be specified by the specific information of the examination from the storing unit.

According to yet another aspect of the present invention, it is provided that an imaging diagnosis supporting method including: receiving, from a user, specific information of an examination to be referred to, and combinations of user identification information and utilization situation information; on the basis of determination information for determining whether to provide predetermined medical information among a plurality of medical information or not for each combination of the user identification information and the utilization situation information, determining whether or not to provide the medical information in the received combination; and when it is determined to provide the medical information, on the basis of the specific information of the examination, collecting the medical information to be provided from a storing unit, which stores a plurality of medical information.

According to yet another aspect of the present invention, it is provided that an imaging diagnosis supporting method including: receiving, from a user, specific information of an examination to be referred to, and combinations of user identification information and utilization situation information; on the basis of first determination information for determining whether to provide an object, which includes at least one of a scan condition, a scan range, and the position of a key image as the ground of diagnosis, and an image, to a user or not for each combination of user identification information and utilization situation information, determining whether or not to provide an object in the received combination; and when, in the determining, it is determined to provide the object, collecting the object to be specified by the specific information of the examination from a storing unit, which stores a plurality of objects each including at least one of a scan condition, a scan range, and the position of a key image as the ground of diagnosis, and an image.

BRIEF DESCRIPTION OF THE SEVERAL VIEWS OF THE DRAWINGS

FIG. 2 is a diagram showing an example of a utilization management table according to the first embodiment;

FIG. 3 is a diagram showing an example of a provision information management table;

FIG. 6 is a flowchart showing a flow of an imaging diagnosis supporting processing according to a second embodiment of the invention;

FIG. 7 is a diagram showing an example of a utilization management table according to the second embodiment;

FIG. 8 is a flowchart showing a flow of an imaging diagnosis supporting processing according to the second embodiment;

FIG. 10 is a flowchart showing a flow of an imaging diagnosis supporting processing according to the third embodiment; and FIG. 11 is a diagram showing an example of a utilization management table according to a fourth embodiment of the invention.

DETAILED DESCRIPTION OF THE INVENTION

Figure 1:
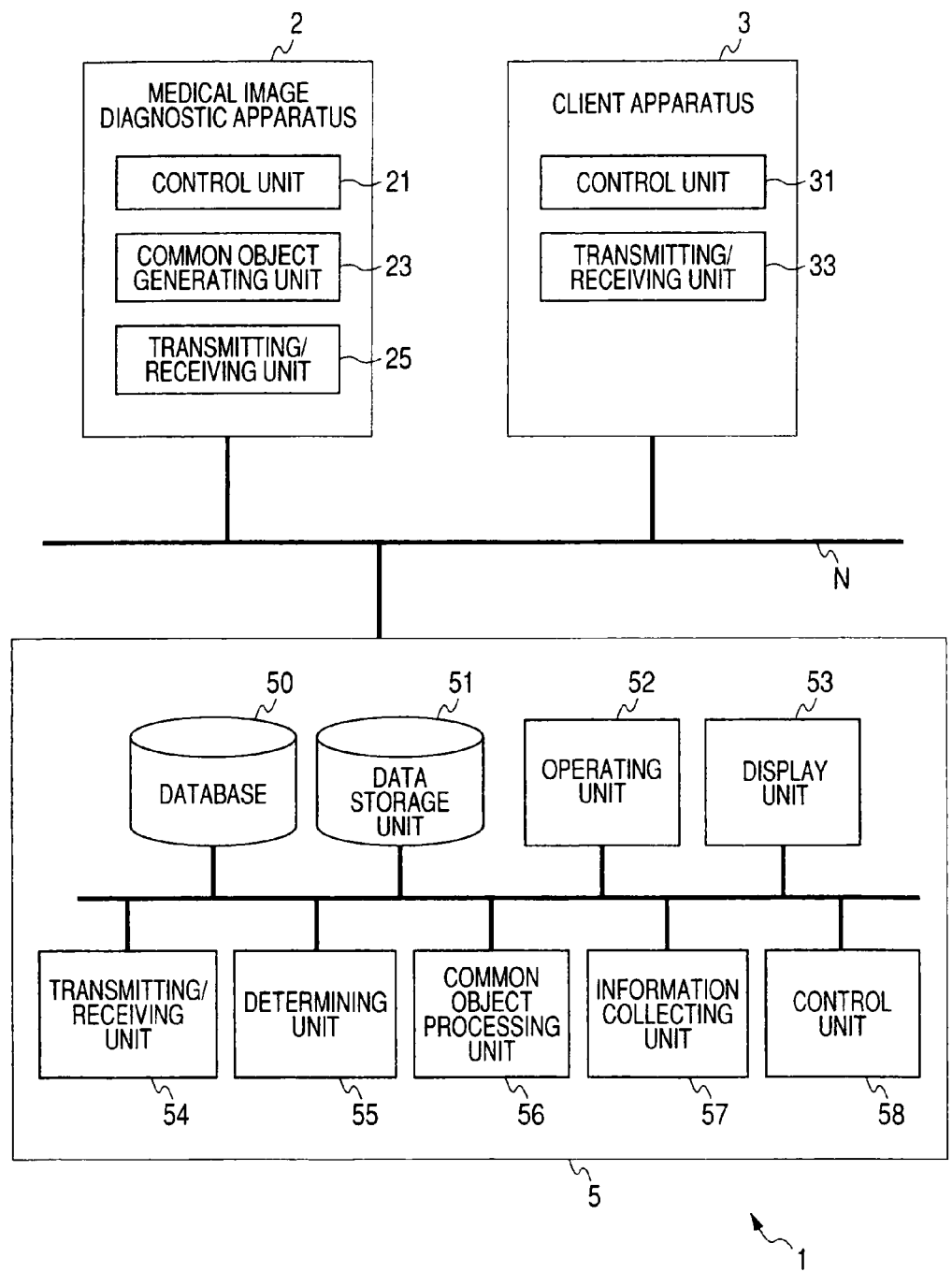
FIG. 1 is a diagram showing the configuration of an in-hospital network system 1, in which an imaging diagnosis supporting system according to a first embodiment of the invention is implemented.

Embodiments of the invention will be described below with reference to the accompanying drawings. In the following description, the same reference numerals are designated to components having the same or similar functions and configurations, and repetitive description will be given only when needed.

In the following embodiments, for concrete explanation, an imaging diagnosis supporting system and an imaging diagnosis supporting method, in which a server apparatus appropriately transmits all or part of contents to a client apparatus, which requires a common object as medical information, will be described. However, the medical information to be handed is not limited to the common object, but the technical spirit of the invention can be applied to medical reports and medical image data.

FIG. 1 is a diagram showing the configuration of an in-hospital network system 1, in which an imaging diagnosis supporting system according to this embodiment is implemented. As shown in FIG. 1, the in-hospital network system 1 includes a medical image diagnostic apparatus 2, a client apparatus 3, and a medical image storing apparatus 5 as a server apparatus.

[Medical Image Diagnostic Apparatus]

The medical image diagnostic apparatus 2 is an image diagnostic apparatus, such as an X-ray computed tomography apparatus (X-ray CT apparatus), a magnetic resonance imaging apparatus, an ultrasonic diagnostic apparatus, a nuclear medicine diagnostic apparatus, or an X-ray diagnostic apparatus. In this embodiment, for concrete explanation, it is assumed that the medical image diagnostic apparatus 2 is an X-ray CT apparatus.

The medical image diagnostic apparatus 2 includes, in addition to an imaging system, which acquires diagnostic images of a patient, a control unit 21, a common object generating unit 23, a transmitting/receiving unit 25, a display unit, a data storage unit, and an operating unit (units with no reference numerals are not shown).

The control unit 21 overall controls the static or dynamic operation of the medical image diagnostic apparatus 2. The common object generating unit 23 generates common objects from image information and collateral information (characters or numeric values) to effectively utilize information (for example, positioning images, scan positions, scan ranges, scan conditions, and image generating conditions) used for past medical treatments. The configuration of the common object will be described below in detail.

The transmitting/receiving unit 25 receives or transmits medical information, such as images or the common objects, from or to another apparatus through a network N.

[Client Apparatus]

The client apparatus 3 requests the server apparatus (in this embodiment, the medical image storing apparatus 5) for the common objects. The client apparatus 3 includes a control unit 31, a transmitting/receiving unit 33, a display unit, a data storage unit, and an operating unit (units with no reference numerals are not shown).

When a request to acquire image information, which was acquired in the past examinations, is transmitted to the medical image storing apparatus 5, the control unit 31 automatically transmits a current user ID (for example, a user ID to be input during login or when the acquisition request is instructed), an apparatus ID for identifying the client apparatus 3, and the name of an application, which is used in the client apparatus 3. In addition, the control unit 31 controls the display unit to display various images and common objects in a predetermined form using data received from the medical image storing apparatus 5.

The transmitting/receiving unit 33 transmits, in response to a predetermined operation, the acquisition request instruction of image information, which was acquired in the past examinations, the current user ID, the apparatus ID, and the application name to the medical image storing apparatus 5. In addition, the transmitting/receiving unit 33 receives processed common object data from the medical image storing apparatus 5.

[Medical Image Storing Apparatus]

The medial image storing apparatus 5 manages and stores the images generated in the medical image diagnostic apparatus 2 by patient IDs and series UIDs. In addition, the medical image storing apparatus 5 analyzes the common objects generated in the medical image diagnostic apparatus 2, and stores various kinds of data in predetermined locations. Furthermore, the medical image storing apparatus 5 operates as an imaging diagnosis supporting system that implements an imaging diagnosis supporting function described below.

The medical image storing apparatus 5 includes a database 50, a data storage unit 51, an operating unit 52, a display unit 53, a transmitting/receiving unit 54, a determining unit 55, a common object processing unit 56, an information collecting unit 57, and a control unit 58.

The database 50 is a database that manages information (whereabouts specific information) for specifying storage locations (whereabouts) of entity data of various images or entity data of the common objects. In addition, the database 50 stores a utilization management table and a provision information management table, which are used for the imaging diagnosis supporting function.

Here, the utilization management table defines whether to provide a common object or not for each of combinations of users and utilization situations, and when the common object is provided, information classifications for determining the contents. In addition, the provision information management table defines contents (provision information) to be included in the common object for each information classification.

FIG. 2 shows an example of the utilization management table. As shown in FIG. 2, in the utilization management table, for each of the combinations of the utilization situations (in this example, application name and used apparatus) and the users, whether to provided a common object or not, and when the common object is provided, the information classifications are defined.

FIG. 3 shows an example of the provision information management table. As shown in FIG. 3, in the provision information management table, the contents to be included in the common object, such as a positioning image, a scan condition, and an image generating condition, is defined for each information classification.

The data storage unit 51 receives various kinds of data, such as image data and common objects, through the transmitting/receiving unit 54, and writes and stores the data in appropriate locations. In addition, when the storage location is decided, deleted, or changed, the data storage unit 51 communicates with the database 50, and corrects common object management information or whereabouts specific information, which is managed by the database 50. Moreover, the data storage unit 51 is not necessarily incorporated in the medical image storing apparatus 5, but it may be provided at a predetermined location on the network.

In this embodiment, the entity data of various images or the whereabouts specific information of the common object is stored in the database 50, and the database 50 receives and stores various kinds of data, such as image data and common objects, received by the data storage unit 51. Of course, this is just an example, but the technical spirit of the invention is not limited to the storage locations of various kinds of data. For example, the database 50 and the data storage unit 51 may be implemented with a single data storage unit. In this way, the storage patterns of various kinds of data may be appropriately changed within the scope of the design items.

The operating unit 52 includes a keyboard, various switches, and a mouse, to which an instruction from an operator can be input.

The display unit 53 is a monitor that displays an operation screen or a predetermined image.

The transmitting/receiving unit 54 receives or transmits the medical information, such as images or common objects, from or to another apparatus through the network N.

The determining unit 55 determines, on the basis of the combination of the user and the utilization situation received through the transmitting/receiving unit 54 and the utilization management table, whether or not to provide a common object in the user and the utilization situation, and when the common object is provided, an information classification. In addition, the determining unit 55 determines provision information corresponding to the information classification on the basis of the determined information classification and the provision information management table.

According to the provision information determined by the determining unit 55, the common object processing unit 56 processes an existing common object to include the provision information.

The information collecting unit 57 collects various kinds of information, which are requested by the client apparatus 3, and the provision information corresponding to the information classification determined in the determining unit 55 from the data storage unit 51 or another apparatus on the network.

The control unit 58 overall controls the static or dynamic operation of the medical image storing apparatus 5.

The control unit 58 develops an exclusive-use program stored in the data storage unit 51 on a memory (not shown), thereby implementing an imaging diagnosis supporting function described below.

(Common Object)

Figure 4:
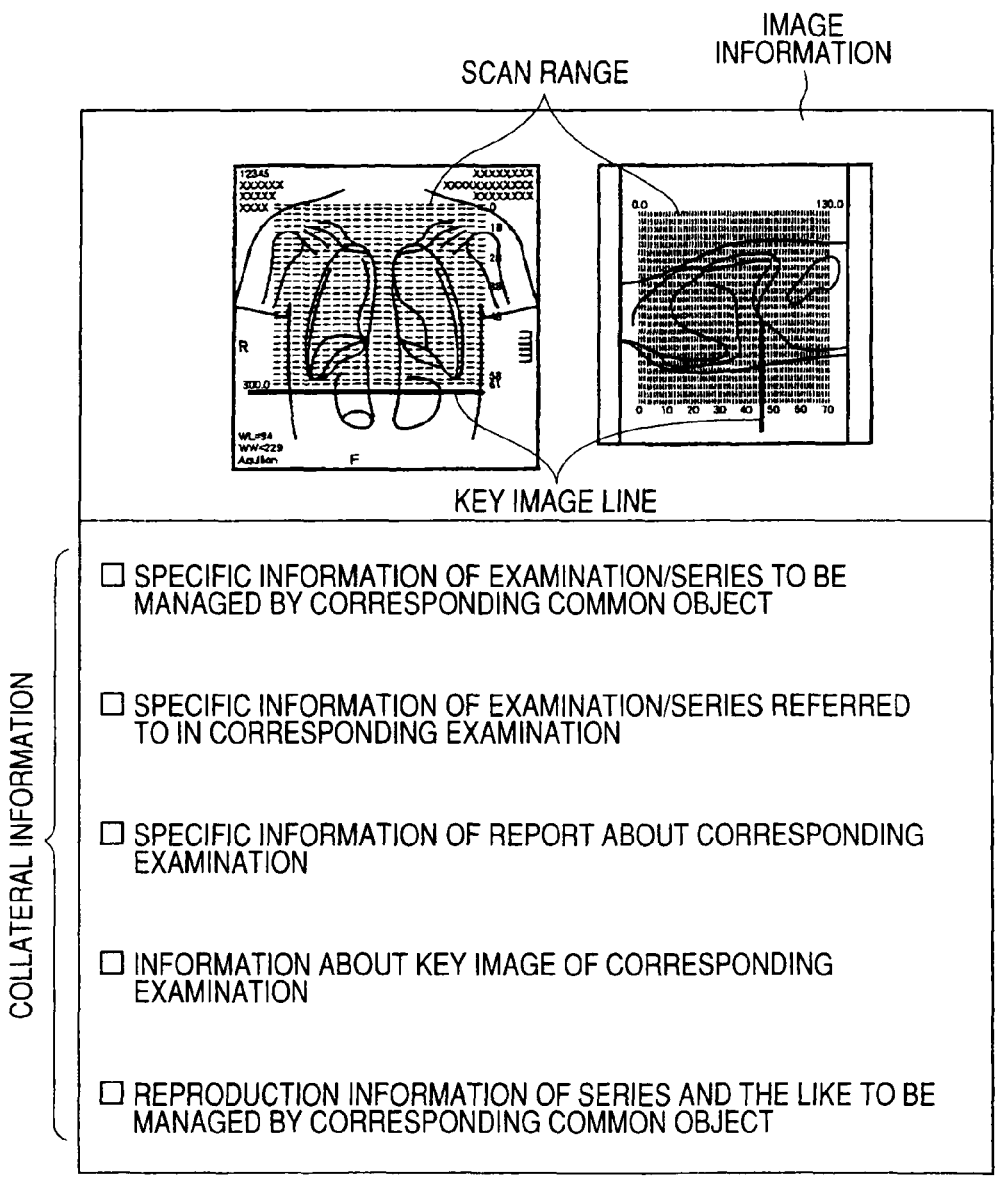
FIG. 4 is a diagram illustrating the configuration of a common object.

Next, the common object will be described. As shown in FIG. 4, the common object is constructed by image information and collateral information (characters or numeric values) to effectively utilize information (for example, positioning images, scan positions, scan ranges, scan conditions, image generating conditions, information about key images, and information about reports) used for past medical treatments. For example, the common object is generated and managed as an image according to the DICOM standard for each examination or series. Moreover, the series is a concept for managing various kinds of information by time (when information is generated), space (where information is generated), and a clinical characteristic of information (clinical meaning).

[Image Information]

Image information of the common object is one or plural positioning images indicative of a position or a range (for example, scannogram used by an X-ray CT apparatus, a coronal section by pilot scan in an MRI apparatus, which is also referred to as "scout view" or "localizer", or the like). The range denotes here a physical range to be detected for signals or to be generated for images by a detector on the basis of energy actually supplied by the medical diagnostic imaging apparatus by X-ray, high frequency, or the like. For example, in case of an X-ray CT apparatus 1, the range is a range (reconstruction range) in a body axis direction to be reconstructed on the basis of projection data detected by the detector. In case of an MRI apparatus, the range is a scan range. Generally, the range is clearly shown by dotted lines or the like on a positioning image to be acquired before scan. The range may be shown along with lines indicative of image generating pitches in the body axis direction. The image information includes a marker indicative of the position of a key image on the positioning image when needed. The image information may further include the key image itself (entity data of the key image).

In the imaging diagnosis supporting function described below, if an edition processing is permitted, the entity data of the key image, the position of the key image on the positioning image, and the like to be managed as the image information are edited according to an edition instruction from a medical report creation supporting apparatus.

[Collateral Information]

The collateral information of the common object may be largely classified into five kinds of information: specific information of examination/series corresponding to the common object, specific information of examination/series to be referred to in an examination, specific information of a report about an examination corresponding to the common object, information about a key image in the examination corresponding to the common object, and reproduction information of the examination/series corresponding to the common object. Hereinafter, each of the five kinds of information will be described.

[Collateral Information 1: Specific Information of Examination/Series Corresponding to Common Object]

This collateral information is information for distinguishing the common object and other common objects. This collateral information includes an identifier (object UID) of the (common) object, a manage series identifier (manage series UID), and a managed examination identifier (managed examination UID).

The object UID is information for distinguishing (specifying) the object from other objects. The object UIDs are generated by a system, which is not used at the time of generating a common object by an object generating unit in each apparatus. The manage series UID and the managed examination UID are information that is used when the common object specifies a series to be managed and an examination to be managed, respectively.

[Collateral Information 2: Specific Information of Examination/Series to be Referred to in Examination]

This collateral information is information indicative of relationship of the common object with other common objects. The collateral information includes a parent (common) object identifier (parent object UID), a related series identifier (related series UID), the series UID, and a related examination identifier.

The parent object UID is information for specifying an object (parent object) to be referred to at the time of generating the object. The related series UID is information for specifying a series using the same conditions (for example, scan conditions, positioning images, and the like) as those of the common object. In some cases, a plurality of related series UIDs are present in the object unique information by its nature. At this time, the collateral information of the series (series date and time, series number, series description, and kind of contrast) and the like are preferably attached in association with the series UID. The series UID is an identifier for specifying the series whose scan condition and the like are indicated by the common object.

Data specified by each UID is linked. Accordingly, by accessing the linked data on the basis of the UID, derivation examination progresses of the image group can be promptly traced. Moreover, creation date and creation time of the common object may be included in the object unique information.

[Collateral Information 3: Specific Information of Report about Examination Corresponding to Common Object]

This collateral information is an identifier (report identifier) for specifying a report generated in the examination. In a predetermined examination, a created report may be corrected at a later day or a new report may be generated. When different identifiers are generated for the reports, all of the report identifiers or a report identifier selected on a predetermined condition may be included.

[Collateral Information 4: Information about Key Image of Examination Corresponding to Common Object]

This collateral information is information (for example, SOPInstanceUID or the like of the DICOM standard) for specifying a key image used for interpretation or imaging diagnosis by a component on the medical image storing apparatus 5 side, and information for specifying the entity data of the key image and the position or direction of the key image (for example, z-axis coordinate position, direction during observation, enlargement ratio, information, such as WW/WL, and the like). When the key image is an MPR image, similarly to the image generating condition, the position or direction, a generating condition, and the like of the MPR image as the key image may be included in the collateral information.

In the imaging diagnosis supporting processing described below, according to a combination of a user who creates a report and an apparatus used to create the report, it is determined whether to perform the edition processing or not, and which kind of an edition processing is performed. Then, according to the determination result, the collateral information is managed.

[Collateral Information 5: Reproduction Information of Examination or Series Corresponding to Common Object]

This collateral information is information for reproducing a processing in the past examination or series, and includes a scan condition, an image generating condition, and the like.

The scan condition is a physical condition necessary to collect physical data from which an image is generated from a patient by scan operation. The contents of this condition depend on the kind of a modality. For example, the scan condition of the X-ray CT apparatus is a physical amount, such as scan start position and range (bed movement amount), KV/mA of an X-ray tube, and a bed movement amount (beam pitch) per rotation with respect to the total width of an image slice to be acquired. However, the contents of the scan condition are not limited to the above examples. For example, a subject insertion direction during an examination (information that a subject is inserted in the apparatus from the feet or the head), whether a contrast medium is administered or not, dose of the contrast medium, the kind of the medium, the body posture of the patient (whether the patient lies with his/her face down or up) may be included. In addition, recently, there is a function of automatically controlling KV/mA such that predetermined image quality is obtained in order to reduce exposure. In such a case, image noise (SD value) as a control amount may be included in the scan condition.

For example, in case of an MRI apparatus, the scan condition may include parameters, such as the scan range, the insertion direction and the posture of a patient, an intensity of magnetic field, a pulse sequence, the kind of a detection coil, the installation position of the detection coil, presence/absence of gate cardio imaging or respiratory gated imaging, presence/absence of air supply to the bed, a body region in the center of scan, and an attachment position.

The image generating condition refers to parameters for reconstructing an image from physical data obtained by scan, i.e., filter process parameters, such as a reconstruction range, a time phase, the position, direction, and thickness of an image, an FOV (enlargement ratio), and a reconstruction function. The image generating condition includes parameters to be used in an image processing, such as volume rendering and MPR process to be executed in various medical image diagnostic apparatuses and image viewing apparatuses. For example, in case of an MPR processing, reference coordinates, a normal vector, a slice thickness, a range, and the like correspond to the parameters.

The range of the reconstruction condition may be defined by attaching a positioning image indicative of a reconstruction range. In this case, a plurality of positioning images indicative of a plurality of reconstruction ranges are stored in a single common object.

Data specified by each UID is linked. Accordingly, by accessing the linked data on the basis of the UID, derivative examination progresses of the image group can be promptly traced. Moreover, creation date and creation time of the common object may be included in the object unique information.

By holding the collateral information, an image that can be compared with the image of last time when interpretation for examination starts can be appropriately acquired without leakage. Moreover, the common object does not necessarily include all of the above-described information. In some cases, the contents of the common object may be changed according to an apparatus to be used or the purpose insofar as the information used for medical treatments can be effectively utilized. For example, a common object used in the medical image diagnostic apparatus (modality) may be constructed by a patient ID, positional information related to a scan range (reconstruction range), collateral information composed of a landmark, and a reference image as image information. In addition, a common object used in the PACS may be constructed by a patient ID, collateral information composed of positional information of a key image and a landmark, and a reference image as image information. When a specification is desired, in which only the past scan conditions can be simply used without needing the reference image, a common object may be constructed by only collateral information including scan conditions.

By holding the collateral information, an image that can be compared with the image of last time when interpretation for examination starts can be appropriately acquired without leakage. Moreover, a common object does not necessarily include all of the above-described information. In some cases, the contents of the common object may be changed according to an apparatus to be used or the purpose insofar as the information used for past medical treatments can be effectively utilized. For example, a common object used in the medical image diagnostic apparatus (modality) may be constructed by a patient ID, positional information related to a scan range (reconstruction range), collateral information composed of a landmark, and a reference image as image information. In addition, a common object used in the PACS may be constructed by a patient ID, collateral information composed of positional information of a key image and a landmark, and a reference image as image information. When a specification is desired, in which only the past scan conditions can be simply used without needing the reference image, a common object may be constructed by only collateral information including scan conditions.

Figure 5:
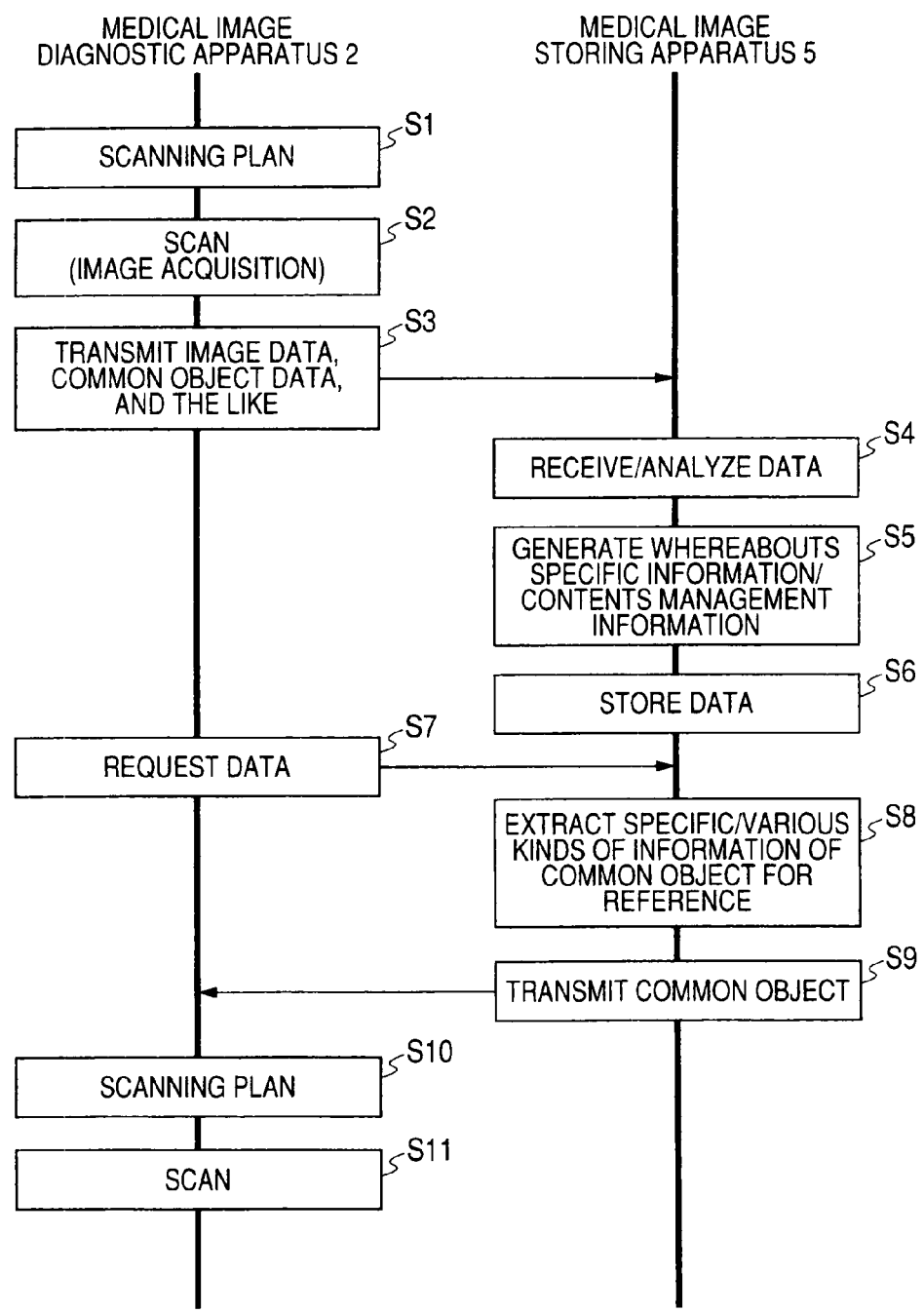
FIG. 5 is a flowchart showing an example a flow of common object generation/management.

FIG. 5 is a flowchart showing an example of a flow of common object generation/management. As shown in FIG. 5, first, the medical image diagnostic apparatus 2 performs a scan plan while referring to past common objects, and scan (image acquisition) (Steps S1 and S2).

The common object generating unit 23 generates a common object on the basis of patient information, the common objects referred to, and the positioning images and the scan conditions for scan. At this time, for distinction from usual image data or for ease of subsequent search, for example, information indicative of a common object may be put into collateral information.

The transmitting/receiving unit 25 transmits image data acquired by scan and data of the generated common object to the medical image storing apparatus 5 through the network (Step S3).

Next, the common object received by the transmitting/receiving unit 54 is analyzed by the information collecting unit 57 (Step S4), such that whereabouts specific information about the common object and common object management information are generated (Step S5). At this time, the entity data of the common object is stored at a predetermined location of the data storage unit 51 (Step S6).

The stored common object is used as reference data at the time of scan at a later date. That is, if a request of common object data is transmitted from the transmitting/receiving unit 25 to the medical image storing apparatus 5 (Step S7), the control unit 58 specifies a common object for reference, for example, on the basis of patient information or the like and common object management information. In addition, the control unit 58 searches the data storage unit 51 using a whereabouts information table, and extracts various kinds of information to be included in the common object (Step S8). The various kinds of extracted information are transmitted to the medical image diagnostic apparatus 2 as the reference common object (Step S9). The medical image diagnostic apparatus 2 receives the common object, performs a scan plan while referring to the common object, and performs scan (image acquisition) (Steps S10 and S11).

(Imaging Diagnosis Supporting Processing)

Next, a processing (imaging diagnosis supporting processing) using an imaging diagnosis supporting function in the medical image storing apparatus 5 according to this embodiment will be described.

FIG. 6 is a flowchart showing a flow of a medical diagnosis supporting processing according to the first embodiment. As shown in FIG. 6, first, the control unit 31 of the client apparatus 3 transmits, for reference in a current examination, an acquisition request of image information and the like acquired in the past examination, a patient ID, an ID for specifying an examination to be referred to, a series ID, and the like to the medical image storing apparatus 5 through the transmitting/receiving unit 33. In addition, the control unit 31 of the client apparatus 3 transmits, along with the acquisition request, a user ID of an operator, an apparatus ID of the client apparatus 3 (for example, station ID, AE (Application Entity), or the like), and the name of an application, which is used in the client apparatus 3, to the medical image storing apparatus 5 through the transmitting/receiving unit 33 (Step S20).

Next, the determining unit 55 of the medical image storing apparatus 5 determines display/non-display of a common object and an information classification on the basis of a combination of the user ID, the apparatus ID, and the application name received from the client apparatus 3 by referring to the utilization management table (Step S21). For example, when "Dr. TARO" (user ID), "INTERPRETATION TERMINAL 1" (apparatus ID), and "COMMON OBJECT VIEWER" (application name) are received from the client apparatus 3 as the combination of the user and the utilization situation, by referring to the utilization management table, the determining unit 55 determines "DISPLAY COMMON OBJECT" and simultaneously determines that the information classification is "ALL". In addition, for example, when "Dr. TARO" (user ID), "INTERPRETATION TERMINAL 1" (apparatus ID), and "DicomVIEWER" (application name) are received from the client apparatus 3 as the combination of the user and the utilization situation, by referring to the utilization management table, the determining unit 55 determines "NOT DISPLAY COMMON OBJECT" and simultaneously determines that the information classification is "NONE".

Next, the determining unit 55 determines provision information corresponding to the information classification (information to be included in the common object) on the basis of the information classification determined at Step S21 and the provision information management table (Step S22). For example, when it is determined at Step S21 that the information classification is "ALL", according to the provision information management table shown in FIG. 3, the determining unit 55 determines that all kinds of the information, such as "POSITIONING IMAGE", "SCAN RANGE", "SCAN CONDITION", "IMAGE GENERATING CONDITION", "EXAMINATION HISTORY", and "INFORMATION ABOUT KEY IMAGE", are provision information. In addition, for example, when it is determined at Step S21 that the information classification is "SCAN CONDITION 1", according to the provision information management table, the determining unit 55 determines that information, such as "POSITIONING IMAGE", "SCAN RANGE", "SCAN CONDITION", and "EXAMINATION HISTORY", are provision information.

Next, the information collecting unit 57 specifies the whereabouts of image data and common object data related to the patient ID, the examination ID, the series ID, and the like received at Step S21 by referring to the database 50. Then, the information collecting unit 57 collects the entity data of the image data and the common object data from the data storage unit 51 or another apparatus through the network when needed (Step S23).

Next, the common object processing unit 56 processes the common object data such that only the provision information determined according to the information classification is included therein (Step S24). For example, if it is determined at Step S22 that "POSITIONING IMAGE", "SCAN RANGE", "SCAN CONDITION", and "EXAMINATION HISTORY" are the provision information to be included in the common object, the common object processing unit 56 deletes or processes, in an unreadable form, the information other than the information corresponding to the four kinds of items. Accordingly, the common object is processed to include only the provision information corresponding to the information classification. Moreover, when information other than the provision information corresponding to the information classification among the information included in the common object is processed in an unreadable form, in view of the communication efficiency of the network, preferably, the processing is performed such that the data size becomes as small as possible. Furthermore, in this embodiment, the information, such as "POSITIONING IMAGE", "SCAN RANGE", "SCAN CONDITION", and "EXAMINATION HISTORY", is held as the collateral information according to the DICOM standard. According to the DICOM standard, the information can be distinguished using the determined identifier and acquired.

Next, the transmitting/receiving unit 54 transmits the collected image data and the processed common object data to the client apparatus 3 through the network (Step S25). In the client apparatus 3, a necessary image is displayed in a predetermined form on the basis of the received image data, and the provision information according to the information classification is displayed in a predetermined form on the basis of the processed common object data (Step S26).

Moreover, when it is determined at Step S21 that the information classification is "NONE", at Steps S22 to S26, a processing about the common object is omitted.

(Advantage)

According to the above-described configuration, the following advantages can be obtained.

According to the imaging diagnosis supporting system 1, whether to provide a common object or not, and when the common object is provided, an information classification are determined by a combination of a user and a utilization situation. Then, the provision information to be included in the common object is determined on the basis of the determined information classification. In addition, the common object is processed to include only the determined provision information, and provided to the client apparatus through the network. Accordingly, when the client apparatus does not requires the common object, the server apparatus does not transmit the common object. Meanwhile, when the client apparatus requires the common object, a common object including only requisite minimum information is provided. For this reason, the user does not need to perform an unnecessary work, such as deletion of useless information, and thus a factor for deterioration of the working efficiency during scan can be excluded. Furthermore, since unnecessary data transmission/reception or a reproduction processing does not need to be performed, a factor for deterioration of the communication efficiency of the network and the operation efficiency of each apparatus can be excluded.

(Second Embodiment)

Next, a second embodiment of the invention will be described.

For example, when a common object is acquired as being used in the current examination, instead of the scan condition or the entity data about the reference image (or information for specifying the entity data), information (for example, UID, information indicative of whereabouts, link information, or the like) (hereinafter, referred to as "related common object specific information") for specifying another common object to be referred to (related common object) may be stored.

In this embodiment, a medical imaging diagnosis supporting system 1 that, in such a case, can further access the related common object and acquire provision information corresponding to an information classification will be described.

FIG. 7 shows an example of a utilization management table according to the second embodiment. The utilization management table according to the second embodiment is different from the utilization management table shown in FIG. 2 in that "GENERATION" is defined for each combination of the user IDs and the utilization situations. Here, "GENERATION" is an index that, when related common object specific information is stored in the acquired common object, with the acquired common object as the first generation, defines to trace and access how old related common objects from the acquired common object to search necessary information.

FIG. 8 is a flowchart showing a flow of an imaging diagnosis supporting processing according to the second embodiment. As shown in FIG. 8, first, the control unit 31 of the client apparatus 3 transmits an acquisition request of image information and the like acquired in the past examination, a patient ID, an examination ID, a series ID, a user ID of an operator, an apparatus ID, and an application name to the medical image storing apparatus 5 through the transmitting/receiving unit 33 (Step S30).

The determining unit 55 of the medical image storing apparatus 5 determines display/non-display of a common object, an information classification, and a generation on the basis of the combination of the user ID, the apparatus ID, and the application name received from the client apparatus 3 by referring to the utilization management table (Step S31). For example, when "Dr. TARO" (user ID), "INTERPRETATION TERMINAL 1" (apparatus ID), and "COMMON OBJECT VIEWER" (application name) are received from the client apparatus 3 as the combination of the user and the utilization situation, by referring to the utilization management table, the determining unit 55 determines "DISPLAY COMMON OBJECT" and simultaneously determines that the information classification is "ALL". In addition, by referring to the utilization management table, the determining unit 55 determines that the generation about the combination is "SECOND GENERATION".

Next, the determining unit 55 determines provision information corresponding to the information classification on the basis of the determined information classification and the provision information management table (Step S32). The information collecting unit 57 specifies the whereabouts of the image data and the common object data related to the patient ID, the examination ID, the series ID, and the like received at Step S21 by referring to the database 50. Then, the information collecting unit 57 collects entity data of image data and common object data from the data storage unit 51 or another apparatus through the network when needed (Step S33).

Next, the determining unit 55 determines whether or not related common object specific information is included in the collected common object (Step S34). As a result, when the related common object specific information is not included, the process progresses to Step S36.

Meanwhile, if it is determined that the related common object specific information is included, the information collecting unit 57 accesses a related common object specified by the related common object specific information, and acquires information included therein (Step S35).

Moreover, if information for specifying a common object to be further referred to is included in the related common object accessed at Step S35, when it is determined at Step S31 that the generation is the third generation, a further access to a related common object is performed.

Next, the common object processing unit 56 processes the common object data to include only the provision information determined according to the information classification (Step S36). The transmitting/receiving unit 54 transmits the collected image data and the processed common object data to the client apparatus 3 through the network (Step S37). In the client apparatus 3, a necessary image is displayed in a predetermined form on the basis of the received image data, and the provision information according to the information classification is displayed in a predetermined form on the basis of the processed common object data (Step S38).

Moreover, if it is determined at Step S31 that the information classification is "NONE", at Steps S32 to S38, a processing about the common object is omitted.

According to the above-described configuration, even if the related common object specific information, instead of the entity data about the scan condition, the reference image, or the like, is stored in the common object to be used, another common object, from which necessary information can be acquired, can be traced, and necessary information can be acquired. Therefore, the same advantages as the first embodiment can be obtained.

(Third Embodiment)

Next, a third embodiment of the invention will be described.

In the first and second embodiments, the server apparatus processes the common object to include only the provision information corresponding to the information classification. In contrast, in this embodiment, on the client apparatus side, display is regulated such that only the provision information corresponding to the information classification among the information included in the common object is displayed.

Figure 9:
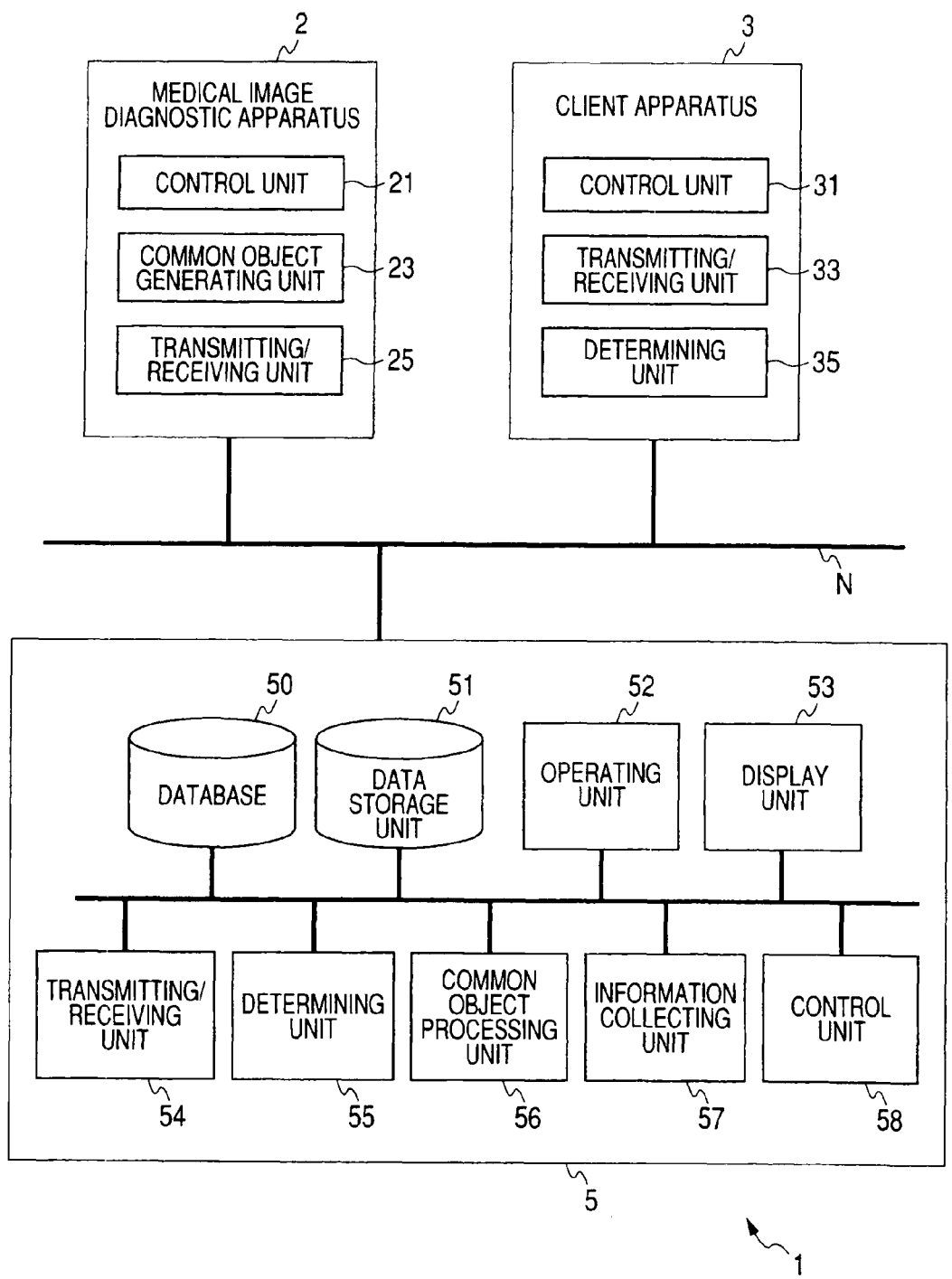
FIG. 9 is a diagram showing the configuration of a medical imaging diagnosis supporting system 1 according to a third embodiment of the invention.

FIG. 9 is a diagram showing the configuration of a medical imaging diagnosis supporting system 1 according to the third embodiment. Compared with the configuration shown in FIG. 1, there is a difference in that the client apparatus 3 further includes a determining unit 35.

The determining unit 35 determines provision information corresponding to the information classification received from the medical image storing apparatus 5 among the information included in the common object received from the medical image storing apparatus 5.

When the common object is displayed, the control unit 31 controls the display unit to display only the provision information corresponding to the information classification determined in the determining unit 35.

FIG. 10 is a flowchart showing a flow of an imaging diagnosis supporting processing according to the third embodiment. As shown in FIG. 10, first, the control unit 31 of the client apparatus 3 transmits an acquisition request of image information and the like acquired in the past examination, a patient ID, an examination ID, a series ID, a user ID of an operator, an apparatus ID, and an application name to the medical image storing apparatus 5 through the transmitting/receiving unit 33 (Step S40).

The determining unit 55 of the medical image storing apparatus 5 determines display/non-display of a common object and an information classification on the basis of a combination of the user ID, the apparatus ID, and the application name received from the client apparatus 3 by referring to the utilization management table (Step S41).

In addition, when it is determined to display the common object, the determining unit 55 determines provision information corresponding to the information classification on the basis of the information classification about the combination and the provision information management table, and generates a list of provision information indicative of the kind of provision information (Step S42). For example, when the information classification is "SCAN CONDITION 1", the determining unit 55 determines that the provision information is "POSITIONING IMAGE", "SCAN RANGE", "SCAN CONDITION", and "EXAMINATION HISTORY", a list of provision information indicating that those four kinds are provision information is generated.

Next, the information collecting unit 57 specifies the whereabouts of the image data and the common object data related to the patient ID, the examination ID, the series ID, and the like received at Step S21 by referring to the database 50. Then, the information collecting unit 57 collects the entity data of the image data and the common object data from the data storage unit 51 or another apparatus through the network when needed (Step S43).

Next, the transmitting/receiving unit 54 transmits the collected image data, common object data, and the like, and the list of provision information to the client apparatus 3 through the network (Step S44).

Next, the determining unit 35 of the client apparatus 3 determines information corresponding to the provision information among the information included in the common object data on the basis of the received list of provision information (Step S45). In addition, the control unit 31 of the client apparatus 3 controls the display unit to display the common object while regulating such that only the provision information corresponding to the information classification among the information included in the common object is displayed.

Moreover, if it is determined at Step S41 that the information classification is "NONE", at Steps S32 to S46, a processing about the common object is omitted.

According to the above-described configuration, the same advantages as the first or second embodiment can also be obtained.

(Fourth Embodiment)

Next, a fourth embodiment of the invention will be described. In this embodiment, the imaging diagnosis supporting processing according to one of the first to third embodiments is performed with a common object and a medical report as medical information to be handled.

FIG. 11 is a diagram showing an example of a utilization management table according to the fourth embodiment. Compared with the utilization management table shown in FIG. 2, there is a difference in that whether a medical report is provided or not and whether only a key image is provided or not are defined for each of the combinations of the user IDs and the utilization situations.

At one of Steps S21, S31, and S41, the determining unit 55 of the medical image storing apparatus 5 determines, in addition to the above-described determination, whether a medical report is provided or not for a combination of a current user and a utilization situation, by referring to the utilization management table shown in FIG. 11. For example, when "Dr. TARO" (user ID), "INTERPRETATION TERMINAL 1" (apparatus ID), and "Dicom VIEWER" (application name) are received from the client apparatus 3 as the combination of the user and the utilization situation, the determining unit 55 determines that the interpretation terminal 1 displays, as an image, an annotation-appended image or a key image assigned by the Key Image Note according to the DICOM standard, and also determines that a medical report is displayed together.

Though not shown, a provision information management table that defines contents (provision information) to be included in a medical report may be generated in advance for each information classification and stored in the database 50 when needed. If so, in the same manner as the common object, as regards a medical report, it is possible to determine information to be included in the medical report to be provided according to the information classification. As a result, even if medical information provided to the client apparatus side includes a medical report, the same advantages as those in the first to third embodiments can be obtained.

The invention is not limited to the foregoing embodiments, but may be embodied by modifying the components without departing from the spirit of the invention. For example, the invention may be modified as follows.

(1) The functions in the embodiments may be realized by installing a program for executing the processing on a computer, such as a workstation and developing the program on a memory. A program that can cause the computer to execute the method may be distributed by being stored in a recording medium, such as a magnetic disk (floppy (Registered Trademark) disk, hard disk, or the like), an optical disk (CD-ROM, DVD, or the like), or a semiconductor memory.

(2) In the foregoing embodiments, the client apparatus 3 and the medical image storing apparatus 5 (server apparatus) are individually provided. However, the invention is not limited thereto, but the functions of the individual apparatuses may be mounted on a single apparatus. In addition, part of the functions of the medical image storing apparatus 5 may be provided in the client apparatus 3, or part of the functions of the client apparatus 3 may be provided in the medical image storing apparatus 5, thereby constructing a server for realizing the imaging diagnosis supporting function.

By properly combining a plurality of components disclosed in the foregoing embodiments, the invention can be variously modified. For example, some of all of the components in the embodiments may be deleted. In addition, the components in different embodiments may be properly combined.

What is claimed is:

1. An imaging diagnosis supporting system, comprising:
a non-transitory memory that stores a plurality of objects each including an image and at least one of a scan condition, a scan range, and a position of a key image as a basis of diagnosis;

a receiving unit configured to receive, from a user, specific information of an examination, and a combination of user identification information and utilization situation information, the utilization situation information indicating how the user will display an object;

a determining unit configured to, based on first determination information that indicates whether to provide the object to the user for various combinations of the user identification information and the utilization situation information, determine whether to provide the object for the received combination;

a collecting unit configured to, when the determining unit determines to provide the object, collect the object specified by the specific information of the examination from the memory; and a display unit configured to display the object specified by the specific information of the examination.

2. The imaging diagnosis supporting system according to claim 1, wherein the determining unit is configured to determine, based on second determination information for determining an information classification for the various combinations of the user identification information and the utilization situation information, the information classification corresponding to the received combination, and to determine, based on third determination information for determining provision information to be included in the object for each information classification, the provision information for the information classification corresponding to the received combination, the imaging diagnosis supporting system further includes a processing unit configured to process the object specified by the specific information of the examination to include only the provision information, and the display unit is configured to display the processed object.

3. The imaging diagnosis supporting system according to claim 1, wherein the determining unit is configured to determine, based on second determination information for determining an information classification for the various combinations of the user identification information and the utilization situation information, the information classification corresponding to the received combination, and to determine, based on third determination information for determining provision information to be included in the object for each information classification, the provision information for the information classification corresponding to the received combination, and the imaging diagnosis supporting system further includes a control unit configured to, when the object specified by the specific information of the examination is displayed, control the display unit to display only the provision information.

4. The imaging diagnosis supporting system according to claim 1, wherein, when information about another object is included in the object specified by the specific information of the examination, the collecting unit is further configured to collect information included in the another object.

5. The imaging diagnosis supporting system according to claim 1, wherein the utilization situation information includes at least one of identification information of an apparatus, which is used by the user to display the object, and a name of an application, which is used in the apparatus used to display the object.

6. The imaging diagnosis supporting system according to claim 1, wherein the image included in the object is a positioning image used to determine at least one of the scan condition and the scan range.

7. An imaging diagnosis supporting server, comprising:

a non-transitory memory that stores a plurality of medical information;

a receiving unit configured to receive, from a user, specific information of an examination, and a combination of user identification information and utilization situation information, the utilization situation information indicating how the user will display an object;

a determining unit configured to, based on determination information that indicates whether to provide predetermined medical information among a plurality of medical information to the user for various combinations of the user identification information and the utilization situation information, determine whether to provide medical information for the received combination; and a collecting unit configured to, when the determining unit determines to provide the medical information, collect the medical information to be provided from the memory, based on the specific information of the examination.

8. The imaging diagnosis supporting server according to claim 7, wherein the medical information is one of a plurality of objects, each of which includes at least one of a scan condition, a scan range, and a position of a key image as a basis of diagnosis, image data acquired in past examinations, and medical reports.

9. An imaging diagnosis supporting server, comprising:

a non-transitory memory that stores a plurality of objects, each including an image and at least one of a scan condition, a scan range, and a position of a key image as a basis of diagnosis;

a receiving unit configured to receive, from a user, specific information of an examination, and a combination of user identification information and utilization situation information, the utilization situation information indicating how the user will display an object;

a determining unit configured to, based on first determination information that indicates whether to provide the object to the user for various combinations of the user identification information and the utilization situation information, determine whether to provide the object for the received combination; and a collecting unit configured to, when the determining unit determines to provide the object, collect the object specified by the specific information of the examination from the memory.

10. The imaging diagnosis supporting server according to claim 9, wherein the determining unit is configured to determine, based on second determination information for determining an information classification for the various combinations of the user identification information and the utilization situation information, the information classification corresponding to the received combination, and to determine, based on third determination information for determining provision information to be included in the object for each information classification, the provision information in the information classification corresponding to the received combination, and the imaging diagnosis supporting server further includes a processing unit configured to process the object specified by the specific information of the examination to include only the provision information.

11. The imaging diagnosis supporting server according to claim 9, wherein the determining unit is configured to determine, based on second determination information for determining an information classification for the various combinations of the user identification information and the utilization situation information, the information classification corresponding to the received combination, and to determine, based on third determination information for determining provision information to be included in the object for each information classification, the provision information in the information classification corresponding to the received combination, and the imaging diagnosis supporting server further includes a providing unit configured to provide only the determined provision information to the user.

12. The imaging diagnosis supporting server according to claim 9, wherein, when information about another object is included in the object specified by the specific information of the examination, the collecting unit is further configured to collect information included in the another object.

13. The imaging diagnosis supporting server according to claim 9, wherein the utilization situation information includes at least one of identification information of an apparatus, which is used by the user to display the object, and a name of an application, which is used in the apparatus used to display the object.

14. The imaging diagnosis supporting server according to claim 9, wherein the image included in the object is a positioning image used to determine at least one of the scan condition and the scan range.

15. An imaging diagnosis supporting method, comprising:

receiving, from a user, specific information of an examination, and a combination of user identification information and utilization situation information, the utilization situation information indicating how the user will display an object;

determining whether to provide predetermined medical information for the received combination, based on determination information that indicates whether to provide the predetermined medical information among a plurality of medical information for various combinations of the user identification information and the utilization situation information; and when it is determined to provide the medical information, based on the specific information of the examination, collecting the medical information to be provided from a storing unit, which stores the plurality of medical information.

16. The imaging diagnosis supporting method according to claim 15, wherein the medical information is one of a plurality of objects, each of which includes at least one of a scan condition, a scan range, and a position of a key image as a basis of diagnosis, image data acquired in past examinations, and medical reports.

17. An imaging diagnosis supporting method, comprising:

receiving, from a user, specific information of an examination, and a combination of user identification information and utilization situation information, the utilization situation information indicating how the user will display an object;

determining whether to provide the object for the received combination, based on first determination information that indicates whether to provide the object, which includes images and at least one of a scan condition, a scan range, and a position of a key image as a basis of diagnosis, to a user for various combinations of user identification information and utilization situation information;

when, in the determining step, it is determined to provide the object, collecting the object specified by the specific information of the examination from a storing unit, which stores a plurality of objects, each including the images and at least one of the scan condition, the scan range, and the position of the key image as the basis of diagnosis.

18. The imaging diagnosis supporting method according to claim 17, wherein the determining step includes determining, based on second determination information for determining an information classification for the various combinations of the user identification information and the utilization situation information, the information classification corresponding to the received combination, and determining, based on third determination information for determining provision information to be included in the object for each information classification, the provision information in the information classification corresponding to the received combination, and the imaging diagnosis supporting method further includes processing the object specified by the specific information of the examination to include only the provision information.

19. The imaging diagnosis supporting method according to claim 18, wherein the determining step includes determining, based on second determination information for determining an information classification for the various combinations of the user identification information and the utilization situation information, the information classification corresponding to the received combination, and determining, based on third determination information for determining provision information to be included in the object for each information classification, the provision information in the information classification corresponding to the received combination, and the imaging diagnosis supporting method further includes providing only the determined provision information to the user.

20. The imaging diagnosis supporting method according to claim 17, wherein, when information about another object is included in the object specified by the specific information of the examination, the collecting step further includes collecting information included in the another object.

21. The imaging diagnosis supporting method according to claim 17, wherein the utilization situation information includes at least one of identification information of an apparatus, which is used by the user to display the object, and a name of an application, which is used in the apparatus used to display the object.

22. The imaging diagnosis supporting method according to claim 17, wherein the image included in the object is a positioning image used to determine at least one of the scan condition and the scan range.

* * * * *